United States Patent [19]

Tomioka et al.

[11] 4,055,715

[45] Oct. 25, 1977

[54] METHOD OF PRODUCING 1-N-[L-(−)-α-HYDROXY-γ-AMINOBUTYRYL]XK-62-2

[75] Inventors: Shinji Tomioka, Machida; Yasuki Mori, Kawasaki; Takashi Nara, Tokyo, all of Japan; Kunikatsu Shirahata, Columbus, Ohio

[73] Assignee: Abbott Laboratories, North Chicago, Ill.

[21] Appl. No.: 542,950

[22] Filed: Jan. 22, 1975

[30] Foreign Application Priority Data

Jan. 24, 1974 Japan .................................. 49-9733

[51] Int. Cl.$^2$ ............................................ C07H 15/22
[52] U.S. Cl. ...................................... 536/17; 424/180

[58] Field of Search .................... 260/210 AB, 210 K; 536/17

[56] References Cited

U.S. PATENT DOCUMENTS

| | | | |
|---|---|---|---|
| 3,780,018 | 12/1973 | Konishi et al. ............... | 260/210 AB |
| 3,781,268 | 12/1973 | Kawaguchi et al. .......... | 260/210 AB |
| 3,796,699 | 3/1974 | Naito et al. .................. | 260/210 AB |
| 3,940,382 | 2/1976 | Umezawa et al. ............ | 260/210 AB |

*Primary Examiner*—Johnnie R. Brown
*Attorney, Agent, or Firm*—Fitzpatrick, Cella, Harper & Scinto

[57] ABSTRACT

1-N-[L-(−)-α-hydroxy-γ-aminobutyryl]XK-62-2 is produced by chemically modifying the antibiotic XK-62-2.

6 Claims, 6 Drawing Figures

METHOD OF PRODUCING 1-N-[L-(−)-α-HYDROXY-γ-AMINOBUTYRYL]XK-62-2

RELATED APPLICATIONS

The present application is broadly related to copending applications Ser. Nos. 531,769 and 531,768 filed Dec. 11, 1974 and assigned to the same assignee as this application, both now abandoned. These applications are directed to certain semi-synthetic derivatives of the antibiotic XK-62-2, including the derivative of the present application.

BACKGROUND OF THE INVENTION

The present invention relates to the production of a semi-synthetic derivative of the antibiotic XK-62-2 and more specifically to the derivative identified as 1-N-[L-(−)-α-hydroxy-γ-aminobutyryl] XK-62-2.

The method for production and the physicochemical properties of the new antibiotic XK-62-2, which is used as the starting material in the present invention, are described in detail in U.S. patent application Ser. No. 364,058 filed on May 25, 1973.

Briefly stated, XK-62-2, is readily produced by culturing actinomycetes such as *Micromonospora sagamiensis*, *Micromonospora echinospora* and *Micromonospora purpurea* by methods usually employed in the culturing of actinomycetes. More specifically, strains of the above mentioned microorganisms are inoculated into a liquid medium containing a carbon source which the microorganism can utilize such as sugars, hydrocarbons, alcohols, organic acids, etc.; inorganic or organic nitrogen sources and additionally inorganic salts and growth promoting factors, and are cultured at 25°–40° C for 2 to 12 days. Isolation and purification of XK-62-2 is carried out by a proper combination of adsorption and desorption from ion exchange resins and active carbon and column chromatography using cellulose, Sephadex and silica gel. In this manner, XK-62-2 can be obtained in the form of the sulfate or in the free form.

XK-62-2 is a basic substance and is obtained as a white powder. XK-62-2 has a molecular formula of $C_{20}H_{41}N_5O_7$, and a molecular weight of 463. The substance is well soluble in water and methanol, slightly soluble in ethanol and acetone and insoluble in chloroform, benzene, ethyl acetate and n-hexane.

SUMMARY OF THE INVENTION

The present invention relates to the production of a new derivative of an antibiotic by chemically modifying a new antibiotic XK-62-2 having the formula:

The modification is carried out by acylating the compound of the above structure with an acylating agent represented by the formula:

(wherein $R_1$ and $R_2$ may be the same or different and are H, OH, $NO_2$, Cl, Br, I, alkyl groups having 1 to 5 carbon atoms or alkoxy groups having 1 to 5 carbon atoms, respectively, $R_3$ is H, F, Cl, Br, I or an alkyl group having 1 to 5 carbon atoms and X is Cl, Br or I), an amino protecting reagent represented by the formula:

(wherein X has the same significance as defined above) or a compound functionally equivalent to said compounds in respect of introducing a readily eliminable protecting group to an amino group to prepare compound II represented by the formula:

[wherein $Y_1$ is

(wherein $R_1$, $R_2$ and $R_3$ have the same significance as defined above); and $Y_2$ and $Y_3$ are hydrogen; $Y_2$ has the same significance as $Y_1$ and $Y_3$ is hydrogen; or $Y_2$ and $Y_3$ form a phthaloyl group],

Compound II above is then acylated with an acylating agent (derived from α-hydroxy-γ-aminobutyric acid) represented by the formula:

[wherein $Y_4$ is H and $Y_5$ is (wherein $R_1$, $R_2$ and $R_3$ have the same significance as defined above) or $Y_4$ and $Y_5$ form a phthaloyl group; and Z is Cl, Br, I or OH]

or a compound functionally equivalent to said acylating agent, to prepare compound III represented by the formula:

(wherein $Y_1$, $Y_2$, $Y_3$, $Y_4$ and $Y_5$ have the same significance as defined above).

The protecting groups $Y_1$, $Y_2$, $Y_3$, $Y_4$ and $Y_5$ are then eliminated in known manner to prepare 1-N-[L-(−)-α-hydroxy-γ-aminobutyryl] XK-62-2 (compound IV) represented by the following formula:

IV and, if desired, further converting compound IV above into pharmaceutically acceptable, non-toxic acid addition salts in a known manner.

The derivative of XK-62-2 of the present invention has a strong antibacterial activity against a variety of Gram-positive and Gram-negative bacteria and particularly exhibits a remarkably strong antibacterial activity against those bacteria that are resistant to the known aminoglycoside antibiotics. Accordingly, the antibiotic of the invention is useful to clean and sterilize laboratory glassware and surgical instruments, and may also be used in combination with various soaps for sanitation purposes and in the cleaning and sanitizing hospital rooms and areas used for the preparation of food. Moreover, the derivative is expected to be effective for the treatment of various infections such as urinary infections and respiratory infections induced by various phlogogenous bacteria.

DESCRIPTION OF THE INVENTION

In accordance with the present invention, 1-N-[L-(−)-α-hydroxy-γ-aminobutyryl] XK-62-2 is prepared by selectively acylating, among the three free amino groups of XK-62-2, the free amino group bonded to the carbon atom at the 1-position, with an α-hydroxy-γ-aminobutyryl group.

First, the amino group bonded to the carbon atom at the 6'-position or those bonded to the carbon atoms at the 2'- and 6'-positions, respectively, which are relatively reactive among the amino groups of XK-62-2, are protected utilizing the difference in reactivity possessed by the amino groups. For this purpose, XK-62-2 is reacted with an acylating agent represented by the formula:

(wherein $R_1$ and $R_2$ may be the same or different and are H, OH, $NO_2$, Cl, Br, I, alkyl groups having 1 to 5 carbon atoms or alkoxy groups having 1 to 5 carbon atoms, $R_3$ is H, F, Cl, Br, I or an alkyl group having 1 to 5 carbon atoms and X is Cl, Br or I), an amino-protecting reagent represented by the formula:

(wherein X has the same significance as defined above) or a compound functionally equivalent to said acylating agent or amino-protecting reagent in respect of introducing a readily eliminable protecting group to an amino group to prepare compound II represented by the formula:

[wherein $Y_1$ is

-continued

(wherein $R_1$, $R_2$ and $R_3$ have the same significance as defined above); and $Y_2$ and $Y_3$ are hydrogen; $Y_2$ has the same significance as $Y_1$ (may be same as or different from $Y_1$) and $Y_3$ is hydrogen; or $Y_2$ and $Y_3$ form a phthaloyl group].

In this case, the protection of the amino groups may be carried out in a usual manner. However, in order to efficiently protect the amino groups bonded to the carbon atoms at the 2'- and 6'-positions, it is desirable to use 1.0 mol to 4.5 mols (0.5 mols to 1.5 mols when the protection of only the amino group bonded to the carbon atom at the 6'-position is desired), preferably, 1.5 mols to 2.6 mols (0.7 mols to 1.2 mols when the protection at the 6'-position only is desired) of the agent per 1 mol of XK-62-2. The reaction is carried out at $-50°$ to $50°$ C, preferably, $-10°$ to $30°$ C for 15 minutes to 24 hours, preferably, 5 to 15 hours. When an increased amount, for example, 3 mols of the protecting substance is used or when the reaction is carried out at an elevated temperature of, for example, 100° C, reaction may proceed but the selectivity of the position to which the protecting group is introduced is greatly reduced. Consequently, the formation ratio of compound II in the reaction mixture is decreased.

(wherein $R_1$, $R_2$ and $R_3$ have the same significance as defined above) or $Y_4$ and $Y_5$ form a phthaloyl group and Z is:

, Cl, Br, I or OH]

(the acylating agent is derived from α-hydroxy-γ-aminobutyric acid) or a compound functionally equivalent to said acylating agent to prepare compound III represented by the formula:

(III)

The solvent for reaction may be at least one selected from the group consisting of tetrahydrofuran, dimethylacetamide, dimethylformamide, lower alcohols, dioxane, ethylene glycol dimethyl ether, pyridine and water.

The thus prepared compound II is then acylated with an acylating agent represented by the formula:

[wherein $Y_4$ is H and $Y_5$ is:

(wherein $Y_1$, $Y_2$, $Y_3$, $Y_4$ and $Y_5$ have the same significance as defined above).

The above-mentioned acylating agents are the compounds which are derived from α-hydroxy-γ-aminobutyric acid. It will be apparent to those skilled in the art that acylating agents having various groups other than Z can be selected to prepare compound III. Accordingly, it is possible within the scope of the present invention to use derivatives of α-hydroxy-γ-aminobutyric acid other than those described above, which are functionally equivalent to the above-mentioned acylating agents for introducing an α-hydroxy-γ-aminobutyryl group to an amino group.

The methods of acylation, where such compounds that are functionally equivalent to the acylating agents are used, are described in M. Bodansky et al: Synthesis, page 453 (1972) and in M. Bodansky et al: Peptide Synthesis, pages 75-135 (1966) (John Wiley & Sons, Inc. U.S.A.).

The above-mentioned acylation reaction is carried out, preferably by using the acylating agent of the formula:

in any one or a mixture of two or more of the solvents selected from tetrahydrofuran, dimethylacetamide, dimethylformamide, lower alcohols, dioxane, ethylene glycol dimethyl ether, pyridine and water, preferably, in a mixture of ethanol and water (2:1) at $-50°$ to $50°$ C, preferably $-20°$ to $20°$ C for 15 minutes to 24 hours, preferably, 5 to 15 hours.

In this case, it is desirable to use 0.5 mols to 1.5 mols, preferably, 0.7 mols to 1.2 mols of the acylating agent per one mol of compound II. When an increased amount, for example, 3 mols of the acylating agent is used, or when the reaction is carried out at an elevated temperature of, for example, $100°$ C, reaction may proceed but the selectivity of the position to which the protecting group is introduced is greatly reduced or, otherwise the acylating agent decomposes. Consequently, the formation ratio of compound III in the reaction mixture is decreased.

The protecting groups $Y_1$, $Y_2$, $Y_3$, $Y_4$ and $Y_5$ of compound III are then eliminated in a known manner to prepare compound IV of the formula:

Undheim et al: Journal of the Chemical Society, Perkin Transactions I, page 829 (1973)].

In a preferred embodiment, the protecting groups are benzyloxy carbonyl groups and elimination is carried out by hydrogenolysis in the presence of a metal catalyst selected from the group consisting of palladium, platinum, rhodium and Raney nickel, preferably, palladium catalyst on a carrier of active carbon; in at least one solvent selected from the group consisting of water, tetrahydrofuran, dimethylacetamide, dimethylformamide, lower alcohols, dioxane, and ethylene glycol dimethyl ether, preferably, in a mixture of water and methanol (1:1), in the presence of a small amount of hydrochloric acid, hydrobromic acid, hydriodic acid or acetic acid; at room temperature and at atmospheric pressure.

If desired, compound IV prepared above may be converted to pharmaceutically acceptable, non-toxic acid addition salts (mono, di-, tri-, tetra or penta salts). In the present invention, non-toxic acid includes inorganic acids such as hydrochloric acid, hydrobromic acid, hydriodic acid, sulfuric acid, phosphoric acid, carbonic acid, etc. and organic acids such as acetic acid, fumaric acid, malic acid, citric acid, mandelic acid, tartaric acid, ascorbic acid, etc. The methods for the production of the acid addition salts are well known in the art.

In the present invention, it is to be understood that in the above-described process, compounds which are not described above may also be used to prepare the intermediate compound II. Such technique will be apparent to those skilled in the art. Such compounds include acylating agents other than described above and aminoprotecting reagents usually used to introduce readily eliminable protecting groups to amino groups. Such (IV)

Elimination is carried out by conventional methods. For example, when the protecting groups form a phthaloyl group, elimination is accomplished with hydrazine; when the protecting groups are carbomethoxy groups or carboethoxy groups, elimination is accomplished with barium hydroxide; when the protecting groups are tertiary butoxy carbonyl groups, elimination is accomplished with formic acid or trifluoroacetic acid; when the protecting groups are trityl groups, elimination is accomplished with acetic acid or trifluoroacetic acid; when the protecting groups are orthonitrophenylsulphenyl groups, elimination is accomplished with acetic acid or hydrochloric acid; and when the protecting groups are chloracetyl groups, elimination is accomplished with 3-nitropyridine-2-thione [reported by K.

readily eliminable protecting group is frequently used in peptide synthesis. The protection of amino groups with such protecting groups and the elimination thereof are described in: M. Bodansky et al: Peptide Synthesis, pages 21-41 (1966) (John Wiley & Sons, Inc. U.S.A.); and A. Kapoor: Journal of Pharmaceutical Sciences, Vol. 59, pages 1-27 (1970).

The semi-synthetic derivative (compound IV) of XK-62-2 of the present invention has an excellent antibacterial activity. It is particularly notable that the derivative has a strong anti-bacterial activity against strains of *Escherichia coli* having R factors which shows resistance to known aminoglycoside antibiotics.

Table 1 illustrates the anti-bacterial spectrum of kanamycin A, gentamicin $C_{1a}$, XK-62-2 and compound IV against various Gram-positive and Gram-negative bacteria measured by agar-dilution method at pH 8.0.

From a comparison of the minimum inhibitory concentration shown in Table 1, it is apparent that compound IV has a strong anti-bacterial activity. Characteristically, the compound shows strong anti-bacterial activity particularly against *Escherichia coli* KY 8327 and 8348.

From the foregoing Table 2, it is apparent that present invention has a very strong antibacterial activity against various bacteria having a resistance to at least one of gentamicin antibiotics and XK-62-2, which produce gentamicin adenyltransferase and/or gentamicin acetyltransferase Type I and Type II intracellularly, thereby inactivating gentamicin antibiotics and XK-62-2.

Moreover, through various protection tests against

Table 1

| Strains | Anti-bacterial Spectrum (Minimum Inhibitory Concentration, mcg/ml) | | | |
|---|---|---|---|---|
| | Kanamycin A | Gentamicin $C_{1a}$ | XK-62-2 | Compound IV |
| *Pseudomonas aeruginosa* BMH 1 | 5.2 | 0.13 | 0.52 | 2.08 |
| *Staphylococcus aureus* ATCC 6538P | 0.021 | 0.004 | 0.088 | 0.016 |
| *Bacillus subtilis* No. 10707 | 0.021 | 0.004 | 0.044 | 0.004 |
| *Proteus vulgaris* ATCC 6897 | 0.16 | 0.033 | 0.033 | 0.065 |
| *Shigella sonnei* ATCC 9290 | 0.16 | 0.033 | 0.033 | 0.033 |
| *Salmonella typhosa* ATCC 9992 | 0.088 | 0.016 | 0.008 | 0.008 |
| *Krebsiella pneumoniae* ATCC 10031 | 0.042 | 0.016 | 0.004 | 0.008 |
| *Escherichia coli* ATCC 26 | 0.16 | 0.033 | 0.016 | 0.004 |
| *Escherichia coli* KY 8327 | 1.04 | 2.08 | 1.04 | 0.016 |
| *Escherichia coli* KY 8348 | 0.041 | 1.04 | 1.04 | 0.004 |

In the foregoing Table 1, *Escherichia coli* KY 8327 and KY 8348 respectively produce gentamicin adenyltransferase and gentamicin acetyltransferase Type I intracellularly. The former bacterium inactivates kanamycins and gentamicins by adenylation, and the latter inactivates gentamicins by acetylation.

Further, the antibacterial spectrum of 1-N-[L-(−)-α-hydroxy-γ-aminobutyryl] XK-62-2 (compound IV) in comparison with kanamycin A, gentamicin C complex ($C_1$, $C_{1a}$ and $C_2$) and XK-62-2 measured by agar dilution method at pH 7.2 is shown in Table 2 below.

infections induced by the strains of the aforementioned resistant bacteria, the compound of the invention is determined to maintain the α-hydroxy-γ-aminobutyryl group in vivo and to exhibit much higher antibacterial activity than the gentamicin antibiotics and XK-62-2.

In administering the compound or its acid addition salts, parenteral administration is preferred with an effective dose of 1.6-6 mg/kg per day.

The acute toxicity ($LD_{50}$) of 1-N-[L-(-)-α-hydroxy-γ-aminobutyryl]XK-62-2 in mice is 250 mg/kg by intravenous injection, while that of XK-62-2 and the gentami- Table 2

| Strains | Antibacterial Spectrum of 1-N-[L-(-)-α-hydroxy-γ-aminobutyryl]XK-62-2 Minimum Inhibitory Concentration (mcg/ml) | | | |
|---|---|---|---|---|
| | Kanamycin A | Gentamicin C complex ($C_1$, $C_{1a}$ and $C_2$) | XK-62-2 | Compound IV |
| *Staphylococcus aureus* 209 P | 0.2 | <0.05 | 0.1 | 0.1 |
| *Staphylococcus aureus* Smith | 0.2 | <0.05 | <0.05 | 0.1 |
| *Bacillus subtilis* ATCC 6633 | 0.2 | <0.05 | <0.05 | 0.1 |
| *Sarcina lutea* ATCC 9341 | 6.25 | 0.2 | 0.4 | 0.4 |
| *Escherichia coli* T-2 | 1.56 | 0.4 | 0.4 | 0.4 |
| *Escherichia coli* T-5 | 1.56 | 0.4 | 0.4 | 0.4 |
| *Escherichia coli* KY 8327[1] | 50 | 12.5 | 12.5 | 0.2 |
| *Escherichia coli* KY 8321[2] | 100 | 6.25 | 3.12 | 0.2 |
| *Escherichia coli* KY 8348[3] | 0.78 | 3.12 | 12.5 | 0.1 |
| *Escherichia coli* KY 8349[4] | >100 | 0.2 | 0.4 | 0.2 |
| *Pseudomonas aeruginosa* BMH 1 | 12.5 | 0.4 | 0.78 | 1.56 |
| *Pseudomonas aeruginosa* KY 8510[5] | 100 | 3.12 | 1.56 | 3.12 |
| *Pseudomonas aeruginosa* KY 8511[6] | 100 | 50 | 100 | 3.12 |
| *Pseudomonas aeruginosa* KY 8512[7] | 12.5 | 0.4 | 0.78 | 0.78 |
| *Pseudomonas aeruginosa* KY 8516[8] | >100 | 3.12 | 3.12 | 3.12 |
| *Providencia sp.* 164[9] | >100 | 50 | 100 | 12.5 |
| *Klebsiella pneumoniae* No. 8045 | 0.4 | 0.2 | 0.1 | 0.2 |
| *Proteus mirabilis* 1287 | 6.25 | 1.56 | 0.78 | 3.12 |
| *Proteus vulgaris* 6897 | 3.12 | 0.78 | 0.78 | 3.12 |
| *Proteus rettgeri* KY 4288 | 0.78 | 0.78 | 0.4 | 0.78 |
| *Proteus morganii* KY 4298 | 1.56 | 0.78 | 0.4 | 0.78 |

[1]produces gentamicin adenyltransferase
[2]produces gentamicin adenyltransferase and neomycin-kanamycin phosphotransferase Type II
[3]produces gentamicin acetyltransferase Type I
[4]produces neomycin-kanamycin phosphotransferase Type I
[5]produces kanamycin acetyltransferase
[6]produces gentamicin acetyltransferase Type I and neomycin-kanamycin phosphotransferase Type I
[7]produces neomycin-kanamycin phosphotransferase Type I and Type II and streptomycin phosphotransferase
[8]probably produces kanamycin acetyltransferase
[9]produces gentamicin acetyltransferase Type II
The foregoing enzymes are produced intracellularly and, with the enzymes, the bacteria inactivate antibiotics.

cin complex (a mixture of $C_1$, $C_{1a}$ and $C_2$) are 93 mg/kg and 72 mg/kg, respectively.

Practice of certain specific embodiments of the present invention is illustrated by the following representative examples.

EXAMPLE 1

Production of 6'-N-carbobenzoxy-XK-62-2

In this example, 2.79 g (6.00mM) of XK-62-2 is dissolved in 50 ml of aqueous 50% dimethylformamide. To the solution is added dropwise a solution of 2.56 g (10.3 mM) of N-benzyloxy-carbonyloxysuccinimide in 40 ml of dimethylformamide with stirring while maintaining the temperature at −5° C to 0° C. The addition is complete in one hour. After the completion of addition, the mixture is allowed to stand overnight at the same temperature. By silica gel thin layer chromatography (developer: isopropanol.concentrated aqueous ammonia.­chloroform = 4:1:1; color reagent: ninhydrin), the presence of by-products and unreacted XK-62-2 in addition to the desired 6'-N-carbobenzoxy-XK-62-2 (Rf: 0.71) is detected in the reaction mixture.

The reaction mixture is then diluted with 30 ml of water and passed through a column having a diameter of 2.5 cm packed with 150 ml of an ion exchange resin, Amberlite CG-50 ($NH_4^+$ form). The column is washed with 200 ml of water. Elution is carried out with 0.1N aqueous ammonia while checking the components by thin layer chromatography. Fractions containing 6'-N-carbobenzoxy-XK-62-2 l as the only component are collected and evaporated to dryness under reduced pressure. As the result, 1.65 g of 6'-N-carbobenzoxy-XK-62-2 is obtained as a colorless amorphous solid. Yield: 44.7%. The thus obtained product is ready for use as the starting material for the subsequent reaction. However, the product can be purified by repeating the above-mentioned column chromatography.

The physicochemical properties of the purified 6'-carbobenzoxy-XK-62-2 are as follows:

Melting point: 108°–110° C

Specific rotation: $[\alpha]_D^{18} = +127.8°$ (C = 0.094, methanol)

Figure 1:
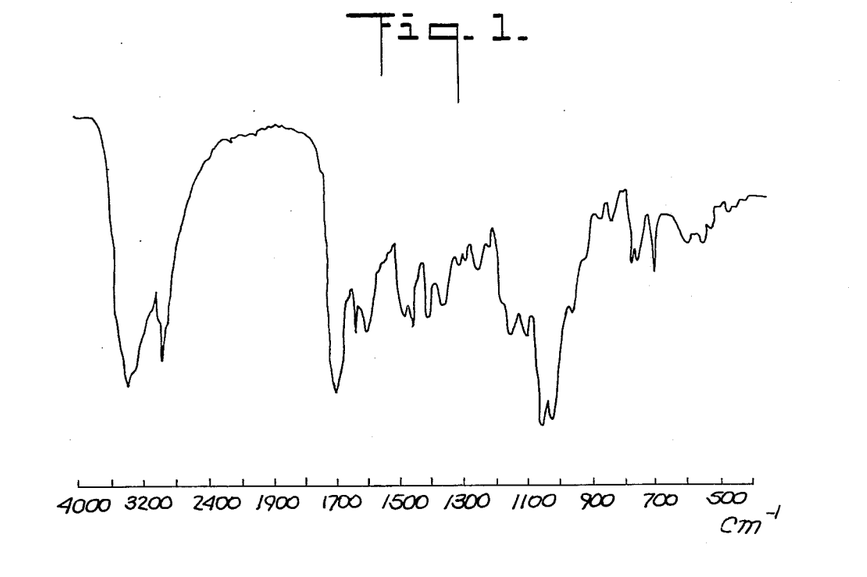

Infrared absorption spectrum (KBr, $cm^{-1}$): 3,700−3,000, 2,930, 1,690, 1,630, 1,596, 1,480, 1,452, 1,402, 1,250, 1,143, 1,096, 1,050, 1,020, 830, 768, 750, 697, 595 and 550 (FIG. 1)

Figure 2:
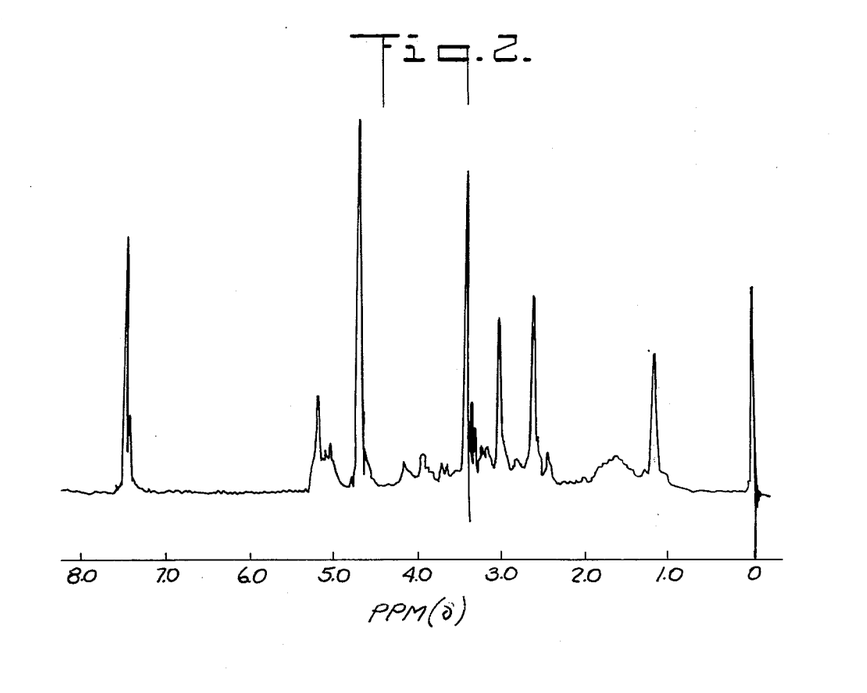

NMR spectrum (methanol −$d_4$) δ (in p.p.m. from TMS): 1.16 (3H, singlet), 2.61 (3H, singlet), 3.01 (3H, singlet), 5.30-4.90(4H, multiplet) and 7.47(5H, singlet) (FIG. 2)

Elementary analysis:

Calculated for $C_{28}H_{47}N_5O_9 \cdot H_2O$: C = 54.77% H = 7.84%;

N = 11.13%.

Found: C = 54.63%; H = 7.97%; N = 11.38%.

EXAMPLE 2

Production of 2'-N, 6'-N-dicabobenzoxy-XK-62-2

In this example, 2.79 g (6.0 mM) of XK-62-2 is dissolved in 20 ml of aqueous 50% dimethylformamide. To the solution is added dropwise a solution of 3.74 g (15.0 mM) of N-benzyloxy-carbonyloxysuccinimide in 20 ml of demethyl-formamide with stirring while maintaining the temperature at 0° to 5° C. The addition is complete in 2 hours. The mixture is allowed to stand at the same temperature overnight. By silica gel thin layer chromatography (developer: isopropanol.concentrated aqueous ammonia.chloroform = 4:1:1; color reagent: ninhydrin), the presence of by-products and unreacted XK-62-2 in addition to the desired 2'-N, 6'-N-dicarbobenzoxy-XK-62-2 (Rf: 0.88) is detected in the reaction mixture.

The reaction mixture is then concentrated under reduced pressure. To the resulting yellow-colored residue are added 50 ml of water and 50 ml of ethylacetate and the mixture is stirred vigorously. The mixture is then allowed to stand to separate into two layers. The water layer is extracted twice each time with 30 ml of ethylacetate. The ethylacetate layer and the ethylacetate extract are combined, dried with anhydrous sodiumsulfate and evaporated to dryness. As the result, 2.58 g of 2'-N-, 6'-N-dicarbobenzoxy-XK-62-2 is obtained as a light yellow amorphous solid. Yield: 61.8%.

The thus obtained product is ready for use as the starting material for the subsequent reaction. However, the product can be purified by a silica gel column chromatography (solvent: isopropanol.concentrated aqueous ammonia. chloroform = 4:1:1).

The physicochemical properties of the purified 2'-N, 6'-N-dicarbobenzoxy-XK-62-2-are as follows:

Melting point: 93° – 95° C

Specific rotation: $[\alpha]_D^{18} = -81.6°$ (C = 0.12, methanol)

Figure 3:
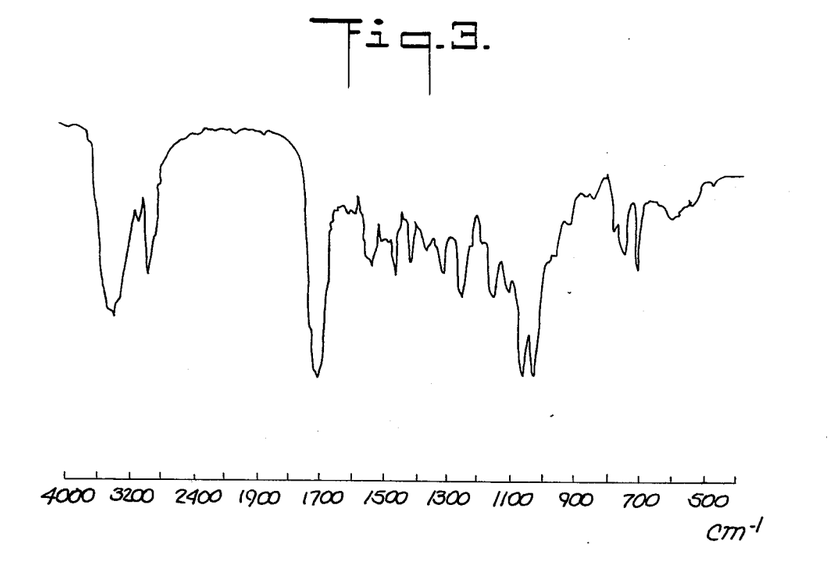

Infrared absorption spectrum (KBr, $cm^{-1}$): 3,800−3,000, 2,950, 1,700, 1,540, 1,456, 1,403, 1,310, 1,250, 1,160, 1,050, 1,010, 960, 738, 700 and 605 (FIG. 3)

Figure 4:
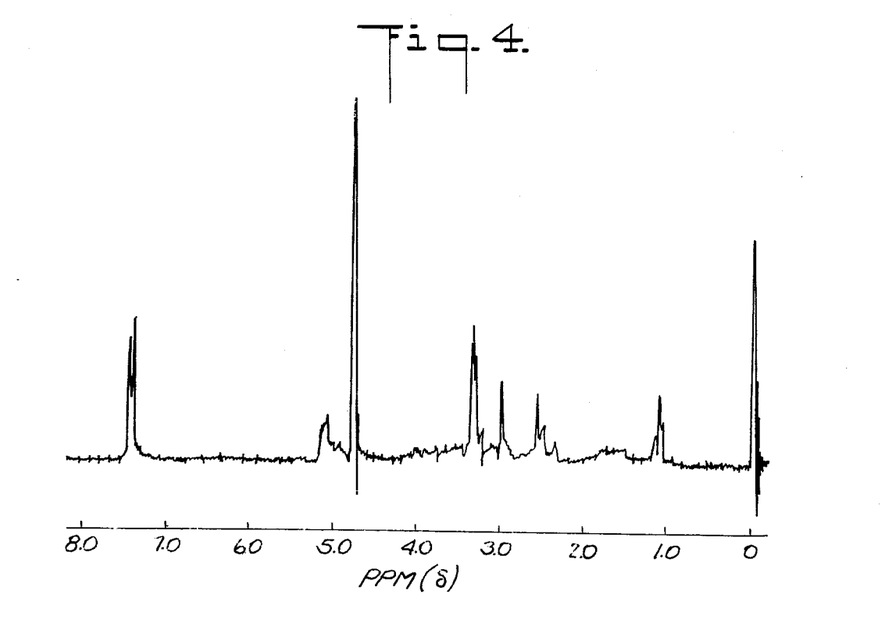

NMR spectrum (methanol −$d_4$) δ (in p.p.m. from TMS): 1.1.3(3H, singlet), 2.62(3H, singlet), 3.01(3H, singlet), 5.30-4.90(6H , broad singlet), 7.43(5H, singlet) and 7.47(5H, singlet) (FIG. 4)

Elementary analysis:

Calculated for $C_{36}H_{55}N_5O_{12} \cdot \frac{1}{2}H_2O$: C = 58.10%; H = 7.29%;

N = 9.46%

Found: C = 58.37%; H = 7.57%; N = 9.46%

EXAMPLE 3

Production of 1-L -N-[L-(-)-α-hydroxy-γ-cabobenzoxy-aminobutyryl]-6'-N-carbobenzoxy-XK-62-2

In this example, 20 ml of a solution of 615 mg (1.0 mM) of 6'-N-carbobenzoxy-XK-62-2 in aqueous 50% tetra-hydrofuran is prepared and cooled to 0° C to −5° C. To the solution is added dropwise, with stirring, 10 ml of a solution of 385 mg (1.1 mM) of N-hydroxysuccinimide ester of L-(-)-α-hydroxy-γ-carbobenzoxyaminobutyric acid in tetrahydrofuran. The ester may be prepared from L-(-)-α-hydroxy-γ-aminobutyric acid by the method described in The Journal of Antibiotics, Vol. 25, p. 695-708, Japan (1972). Further, L-(-)-α-hydroxy-γ-aminobutyric acid may be prepared by the method described in Tetrahedron Letters, p. 2625-2628 (1971). The addition is complete in one hour. After the completion of addition, the mixture is allowed to react overnight. By silica gel thin layer chromatography under the same conditions as described in Example 1, the presence of small amounts of by-products and unreacted starting material, 6'-N-carbobenzoxy-XK-62-2 is detected in addition to 1-N-[L-(-)α-hydroxy-γ-carbobenzoxyaminobutyryl]-6'-N-carbobenzoxy-XK-62-2 (Rf: 0.85) in the reaction mixture.

The reaction mixture is then concentrated under reduced pressure to obtain 1.12 g of a slightly yellow residue. The residue contains N-hydroxysuccinimide and L-(-)-α-hydroxy-γ-carbobenzoxyaminobutyric acid in addition to the components detected above but the residue is used for the subsequent reaction without purication. If desired, 1-N-[L-(-)-α-hydroxy-γ-carbobenzoxyaminobutyryl]-6'N -carbobenzoxy-XK-62-2 can be isolated and purified by column chromatography using an ion exchange resin under the same conditions as described in Example 1.

EXAMPLE 4

Production of
1-N-[L-(-)-α-hydroxy-γ-carbobenzoxy-aminobutyryl-2'-N, 6'-N-dicarbobenzoxy-XK-62-2

In this example, 20 ml of a solution of 740 mg (1.0 mM) of 2'N, 6'-N-dicarbobenzoxy-XK-62-2 in aqueous 50% dimethyl-formamide is prepared and cooled to 0° to −5° C. To the solution is added dropwise 10 ml of a solution of 385 mg (1.1 mM) of N-hydroxysuccinimide ester of L-(-)-α-hydroxy-γ-carbobenzoxyaminobutyric acid in dimethylformamide with stirring. The addition is complete in one hour. After the completion of addition, the mixture is allowed to react overnight. By silica gell thin layer chromatography under the same conditions as described in Example2, the presence of small amounts of by-products and unreacted starting material, 2'-N, 6'-N-dicarbobenzoxy-XK-62-2 is detected in addition to 1-N-[L-(-)-α-hydroxy-γ-carbobenzoxyaminobutyryl]-2'-N, 6'-N-dicarbobenzoxy-XK-62-2 (Rf: 0.93) in the mixture.

The reaction mixture is concentrated under reduced pressure to obtain 1.32 g of a slightly yellow residue. The residue contains N-hydroxysuccinimide and L-(-)-α-hydroxy-γ-carbobenzoxyaminobutyric acid in addition to the components detected above, but the residue is used for the subsequent reaction without purification. If desired, 1-N-[L-(-)-α-hydroxy-γ-carbobenzoxyaminobutyryl]-2'-N, 6'-N-dicarbo-benzoxy-XK-62-2 can be isolated and purified by silica gel column chromatography under the same conditions as described in Example 2.

EXAMPLE 5

Production of
1-N-[L-(-)-αhydroxy-γ-aminobutyryl]-XK-62-2

In this example, 1.12 g of the crude product obtained in Example 3 containing 1-N-[L-(-)-α-hydroxy-γ-carbobenzoxyaminobutyryl]-6'-N-carbobenzoxy-XK-62-2 as a main component is dissolved in 20 ml of aqueous 20% methanol. To the solution is added 1 ml of acetic acid and the mixtureis then subjected to hydrogenolysis in the presence of 130 mg of 5% active carbon-palladium catalyst at room temperature and at atmospheric pressure for 6 hours.

By silica gel thin layer chromatography using isopropanol.concentrated aqueous ammonia. chloroform (2:1:1), the presence of 1-N-[L-(-)-α-hydroxy-γ-aminobutyryl]-XK-62-2 (Rf: 0.40), the positional isomers thereof and a small amount of XK-62-2 (due to the unreacted starting material contained in the crude product of Example 3) is detected.

The catalyst is separated by filtration and the filtrate is concentrated under reduced pressure. The resulting residue is then dissolved in 10 ml of water. The solution is passed through a column having a diameter of 1.5 cm packed with 70 ml of an ion exchange resin, Amberlite CG-50 (NH$_4$+form). The column is washed with 200 ml of water. Then, 0.2N aqueous ammonia is passed through thecolumn to recover XK-62-2 1 (105 mg).

Then, elution is carried out with 0.4N aqueous ammonia while checking the components by thin layer chromatography. Fractions containing 1-N-[L-(-)-α-hydroxy-γ-aminobutyryl]-XK-62-2 as the only component are collected and evaporated to dryness under reduced pressure. As the result, 292 mg of a colorless amorphous solid is obtained. Yields: 41.3% from 6'-N-carbobenzoxy-XK-62-2.

Figure 5:
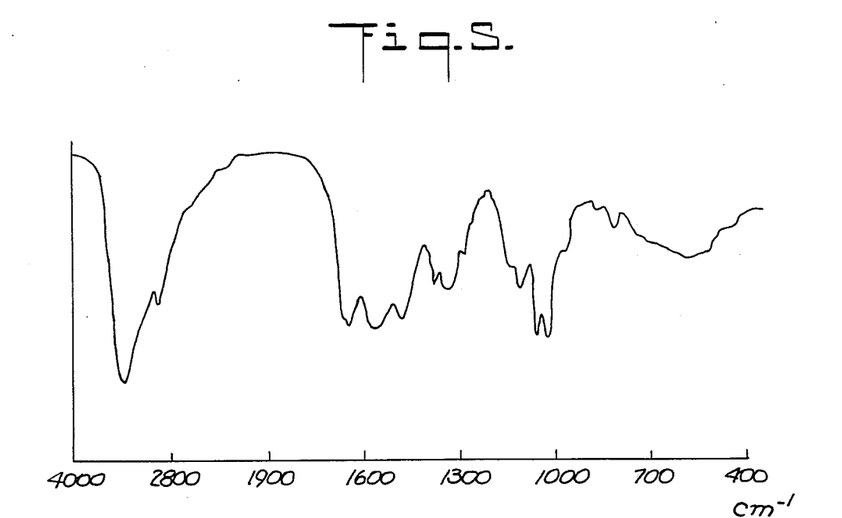

Melting point: 120°– 124° C
Specific rotation: $[\alpha]_D^{29}$ = +99.0° (C = 0.10, water)
Infrared absorption spectrum (KBr, cm$^{-1}$): 3,700–3,100, 2,940, 1,640, 1,565, 1,480, 1,385, 1,340, 1,282, 1,111, 1,054, 1,022, 973, 816 and 700-600 (FIG. 5).

Figure 6:
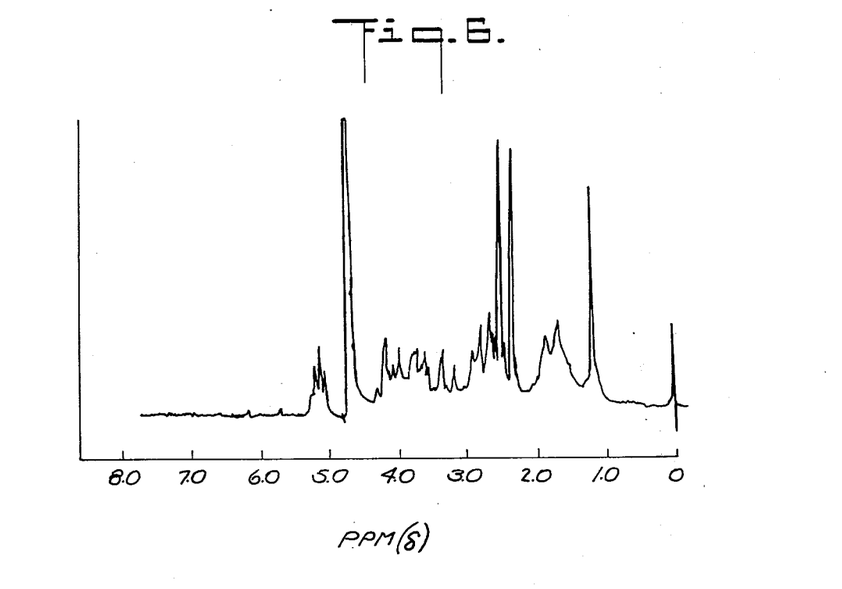

NMR spectrum (D$_2$O) δ (in p.p.m. from DSS): 1.20(3H, singlet) 2.36(3H, singlet), 2.52(3H, singlet), 5.14(1H, doublet, J = 4.0Hz) 5.22(1H, doublet, J = 4.0Hz) (FIG. 6)

Elementary analysis: Calculated for C$_{24}$H$_{48}$N$_6$O$_9$.½H$_2$CO$_3$: C = 49.39%; H = 8.29%; N = 14.11%
Found: C = 48.96%; H = 8.37%; N = 13.95%

EXAMPLE 6

Production of
1-N-[L-(−)-α-hydroxy-γ-aminobutyryl]XK-62-2

In this example, 1.32 g of the crude product obtained in Example 4 containing 1-N-[L-(−)-α-hydroxy-γ-carbobenzoxyaminobutyryl]-2'-N, 6'N-dicarbobenzoxy-XK-62-2 as a main component is dissolved in 20 ml of aqueous 20% methanol. To the solution is added 2 ml of acetic acid and the mixture is then subjected to hydrogenolysis in the presence of 150 mg of 5% active carbon-palladium catalyst at room temperature and at atmospheric pressure for 6 hours. By silica gel thin layer chromatography (developer: isopropanol.concentrated aqueous ammonia.chloroform = 2:1:1; color reagent: ninhydrin), the presence of 1-N-[L-(−)-α-hydroxy-γ-aminobutyryl]-XK-62-2 Rf: (0.40), its positional isomers and a small amount of XK-62-2 (due to unreacted 2'-N-, 6'-N-dicarbobenzoxy-XK-62-2 in Example 4) is detected.

The catalyst is separated by filtration and the filtrate is concentrated under reduced pressure. The resulting residue is then dissolved in 10 ml of water and passed through a column having a diameter of 1.5 cm packed with 70 ml of an ion exchange resin, Amberlite CG-50 (NH$_4$+ form). The column is washed with 20 ml of water. Then, 0.2N aqueous ammonia is passed through the column to recover XK-62-2 (87 mg). Thereafter, elution is carried out with 0.4N aqueous ammonia while checking the components by thin layer chromatography. Fractions containing 1-N-[L-(−)-α-hydroxy-γ-aminobutyryl]-XK-62-2 as the only component are collected and evaporated to dryness under reduced pressure. As the result, 495 mg of a colorless amorphous solid is obtained. Yield: 70.2% from 2'-N, 6'-N-dicarbobenzoxy-XK-62-2.

Melting point: 120°-124° C
Specific rotation: $[\alpha]_D^{29}$ = +99.0° (c = 0.10, water)
Infrared absorption spectrum (KBr, cm$^{-1}$): 3,700-3,100, 2,940, 1,640, 1,565, 1,480, 1,385, 1,340, 1,282, 1,111, 1,054, 1,022, 973, 816and 700–600 (FIG. 5)

NMR spectrum (in D$_2$O) δ (in p.p.m. from DSS): 1.20(3H, singlet), 2.36(3H, singlet), 2.52(3H, singlet), 5.14(1H, doublet, J = 4.0Hz), 5.22(1H, doublet, J = 4.0Hz) (FIG. 6)

Elementary analysis: Calculated for: $C_{24}H_{48}N_6O_9 \cdot \frac{1}{2} H_2CO_3$: C = 49.39%; H = 8.29%; N = 14.11%
Found: C = 48.96%; H = 8.37%; N = 13.95%

EXAMPLE 7

Production of
1-N-[L-(−)-α-hydroxy-γ-aminobutyryl]-XK-62-2

In this example, 112 mg (0.97 mM) of N-hydroxy-succinimide and 242 mg (0.97 mM) of L-(−)-α-hydroxy-γ-phthalimidebutyric acid are dissolved in 20 ml of tetrahydrofuran. [L-(−)-α-hydroxy-δ-phthalimidebutyric acid can be prepared by the method described in The Journal of Antibiotics, Vol. 25, p. 741–742, Japan (1972)]. To the solution is added 200 mg (0.97 mM) of dicyclohexylcarbodiimide with stirring under ice-cooling. After 1 hour, dicyclohexylurea which separates from the solution is removed by filtration. The filtrate is added to 10 ml of a solution of 461 mg (0.75 mM) of 6'-N-carbobenzoxy-XK-62-2 in aqueous 50% tetrahydrofuran. The addition is complete in 30 minutes. After the completion of addition, the mixture is allowed to stand overnight. The reaction mixture is concentrated under reduced pressure and the separated dicyclohexylurea is removed by filtration. The residue is then dissolved in 10 ml of 50% ethanol containing 10% hydrazine and the solution is allowed to react at 60° C for 3 hours to eliminate the phthaloyl group. Then, 1 ml of acetic acid, 10 ml of ethanol and 200 mg of 5% active carbon-palladium catalyst are added to the solution. The mixture is subjected to hydrogenolysis at room temperature and at atmospheric pressure for 14 hours to eliminate the carbobenzoxy group. The catalyst is separated by filtration and the filtrate is concentrated under reduced pressure. The residue is dissolved in 10 ml of water and the solution is passed through a column having a diameter of 1.5 cm packed with 80 ml of an ion exchange resin, Amberlite CG-50 ($NH_4^{30}$ form). The column is washed with water. Elution is then carried out with 0.4N aqueous ammonia while checking the components by silica gel thin layer chromatography. Fractions containing 1-N-[L-(−)-α-hydroxy-γ-aminobutyryl]-XK-62-2 as the only component are collected and evaporated to dryness under reduced pressure. As the result, 206 mg of a colorless product is obtained. Yield: 38.9%.

EXAMPLE 8

Production of
1-N-[L-(−)-α-hydroxy-γ-aminobutyryl]-XK-62-2

In this example, 112 mg (0.97 mM) of N-hydroxy-succinimide and 242 mg (0.97 mM) of L-(−)-α-hydroxy-γ-phthalimidebutyric acid are dissolved in 20 ml of tetrahydrofuran. To the solution is added 200 mg (0.97 mM) of dicyclohexylcarbodiimide with stirring under ice-cooling. After one hour, dicyclohexylurea which separates from the solution is removed by filtration and the filtrate is added to 10 ml of a solution of 555 mg (0.75 mM) of 2'-N, 6'-N-dicarbobenzoxy-XK-62-2 in aqueous 50% tetrahydrofuran. The addition of complete in 30 minutes. The mixture is allowed to stand overnight. The reaction mixture is then concentrated under reduced pressure and the separated dicyclohexylurea is removed by filtration. The resulting residue is dissolved in 10 ml of 50% ethanol containing 10% hydrazine and the solution is allowed to react at 60° C for 3 hours to eliminate the phthaloyl group. Then 1 ml of acetic acid, 10 ml of ethanol and 200 mg of 5% active carbon-palladium catalyst are added to the reaction mixture and the resulting mixture is subjected to hydrogenolysis at room temperature and at atmospheric pressure for 16 hours to eliminate the carbobenzoxy group. The catalyst is separated by filtration and the filtrate is concentrated under reduced pressure. The residue is dissolved in 10 ml of water and then passed through a column having a diameter of 1.5 cm packed with 80 ml of an ion exchange resin, Amberlite CG-50 ($NH_4^{30}$ form). The column is washed with water. Elution is carried out with 0.4N aqueous ammonia while checking the components by thin layer chromatography. The fractions containing 1-N-[L-(−)-α-hydroxy-γ-aminobutyryl]-XK-62-2 as the only component are collected and evaporated to dryness under reduced pressure. As the result, 324 mg of a colorless product is obtained. Yield: 61.2%.

EXAMPLE 9

Production of
1-N-[L-(−)-α-hydroxy-γ-aminobutyryl]-XK-62-2 monosulfate

In this example, 7.06 g (10 mM) of 1-N-[L-(−)-α-hydroxy-γ-aminobutyryl]-XK-62-2 is dissolved in 20 ml of water. To the solution is added a solution of 0.98 g (10 mM) of sulfuric acid in 5 ml of water under cooling. After 30 minutes, cold ethanol is added to the mixture until precipitation is complete. The precipitate white solid is recovered by filtration to obtain 1-N-[L-(−)-α-hydroxy-γ-aminobutyryl]-XK-62-2 monosulfate.

What is claimed is:

1. A process for producing a compound of the formula:

which comprises reacting a compound of the formula:

with an acylating agent selected from the group consisting of:

wherein $R_1$ and $R_2$ may be the same or different and are H, OH, $NO_2$, Cl, Br, I, alkyl groups having 1 to 5 carbon atoms or alkoxy groups having 1 to 5 carbon atoms, respectively, $R_3$ is H, F, Cl, Br, I or an alkyl group having 1 to 5 carbon atoms and X is Cl, Br or I; or an amino protecting reagent selected from the group consisting of:

wherein X has the same significance as defined above to introduce an eliminable protecting group to the amino group bound to the carbon atoms at the 2' and 6' positions to prepare a first intermediate compound represented by the formula wherein $Y_1$ is wherein $R_1$, $R_2$ and $R_3$ have the same significance as defined above, $Y_2$ has the same significance as $Y_1$ and $Y_3$ is hydrogen, or $Y_2$ and $Y_3$ form a phthaloyl group; acylating said first intermediate compound with an acylating agent derived from α-hydroxy-γ-aminobutyric acid represented by the formula:

wherein $Y_4$ is H and $Y_5$ is wherein $R_1$, $R_2$ and $R_3$ have the same significance as defined above or $Y_4$ and $Y_5$ form a phthaloyl group; and Z is to prepare a second intermediate compound represented by the formula:

wherein $Y_1$, $Y_2$, $Y_3$, $Y_4$ and $Y_5$ have the same significance as defined above; and thereafter eliminating said protecting groups wherein said reaction to prepare said first intermediate compound is carried out at a temperature from $-50°$ to $50°$ C for from ¼ to 24 hours and wherein from 1.0 to 4.5 moles of said acylating agent having the formula or said amino protecting reagent is employed per mole of and wherein said first intermediate compound is acylated to prepare said second intermediate compound at a temperature from $-50°$ to $50°$ C for from ¼ to 24 hours employing 0.5 to 1.5 moles of said acylating agent having the formula per mole of said first intermediate compound.

2. A process according to claim 1 which includes the additional step of converting said compound to a pharmaceutically acceptable non-toxic, acid addition salt thereof.

3. A process according to claim 1 wherein said acylation step is carried out with an acylating agent represented by the formula:

4. A process according to claim 3 wherein said acylation step is carried out in at least one solvent selected from the group consisting of tetrahydrofuran, dimethylacetamide, dimethylformamide, lower alcohols, dioxane, ethylene glycol dimethyl ether, pyridine and water.

5. A process according to claim 4 wherein said solvent is a mixture of ethanol and water and said acylation is carried out at $-20°$ to $20°$ C.

6. A process according to claim 1 wherein said reaction step to produce said first intermediate compound is carried out in a solvent selected from the group consisting of tetrahydrofuran, dimethylacetamide, dimethylformamide, lower alcohols, dioxane, ethylene glycol dimethyl ether, pyridine and water.

* * * * *

UNITED STATES PATENT OFFICE
CERTIFICATE OF CORRECTION

Patent No. 4,055,715            Dated October 25, 1977

Inventor(s) Shinji Tomioka, et al.

It is certified that error appears in the above-identified patent and that said Letters Patent are hereby corrected as shown below:

Col. 13, line 9, "(6.00 mM)" should be --(6.0 mM)--;

line 30, "1" should be omitted;

line 38, "6'-car-" should be --6'-N-car- --;

line 57, "N-dicabobenzoxy" should be --N-dicarbo-benzoxy--;

Col. 14, line 25, "-81.6°" should be --+81.6°--;

line 31, "1.1.3" should be --1.13--;

line 41, delete "-L";

line 42, "cabobenzoxy" should be --carbobenzoxy--;

UNITED STATES PATENT OFFICE
CERTIFICATE OF CORRECTION

Patent No. 4,055,715          Dated October 25, 1977

Inventor(s) Shinji Tomioka, et al.

It is certified that error appears in the above-identified patent and that said Letters Patent are hereby corrected as shown below:

Col. 15, line 44, "αhydroxy" should be --α-hydroxy--;

line 68, "XK-62-2 1" should be --XK-62-2--;

Col. 17, line 11, "hydroxy-δ-phthal" should be --hydroxy-γ-phthal--;

line 37, "($NH_4^{30}$) should be --$NH_4^+$--;

line 59, "addition of complete" should be --addition is complete--;

Col. 18, line 11, "($NH_4^{30}$ form) should be --($NH_4^+$ form)--.

Signed and Sealed this

Seventh Day of February 1978

[SEAL]

Attest:

RUTH C. MASON
*Attesting Officer*

LUTRELLE F. PARKER
*Acting Commissioner of Patents and Trademarks*